United States Patent [19]
Watanabe et al.

[11] Patent Number: 5,349,107
[45] Date of Patent: Sep. 20, 1994

[54] PROCESS FOR PRODUCING OPTICALLY ACTIVE γ-HYDROXYKETONES

[75] Inventors: Seiji Watanabe; Shigeru Mitsuhashi; Hidenori Kumobayashi, all of Hiratsuka, Japan

[73] Assignee: Takasago International Corporation, Tokyo, Japan

[21] Appl. No.: 130,173

[22] Filed: Oct. 1, 1993

[30] Foreign Application Priority Data

Oct. 5, 1992 [JP] Japan .................. 4-265879

[51] Int. Cl.$^5$ .................................. C07C 45/64
[52] U.S. Cl. .......................... 568/318; 568/315; 568/316; 568/396; 568/392; 568/394
[58] Field of Search ............. 568/396, 862, 392, 315, 568/316, 394, 318

[56] References Cited

U.S. PATENT DOCUMENTS 4,916,252 4/1990 Sayo et al. ................ 568/862
5,066,815 11/1991 Sayo et al. ................ 568/862

OTHER PUBLICATIONS

Bull. Soc. Chim. Belg., vol. 100, No. 8, 1991, H. Brunner, et al., "Asymmetrische Katalysen, 69 [1] Enantioselektive Hydrierung von Dicarbonylverbindungen Mit NaBr/L-(+)-Weinsaure Modifizierten Nickelkatalysatoren", pp. 585–595.

*Primary Examiner*—James H. Reamer
*Attorney, Agent, or Firm*—Oblon, Spivak, McClelland, Maier & Neustadt

[57] ABSTRACT

Disclosed herein is a process for producing a γ-hydroxyketone (2), which comprises asymmetrically hydrogenating a γ-diketone (1) in the presence of a ruthenium-optically active phosphine complex as a catalyst

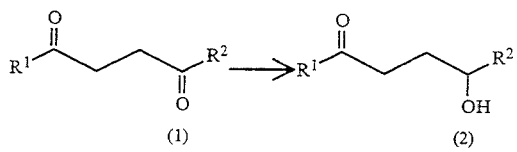

wherein $R^1$ and $R^2$ mean individually an alkyl or phenyl group which may have a substituent group. According to the invention, optically active γ-hydroxyketones useful in synthesizing optically active moiety in, biodegradable polymers, perfumes, intermediates for synthesizing medicines and the like can be efficiently prepared.

14 Claims, No Drawings

PROCESS FOR PRODUCING OPTICALLY ACTIVE γ-HYDROXYKETONES

BACKGROUND OF THE INVENTION i) Field of the Invention

The present invention relates to a process for producing optically active γ-hydroxyketones which can be used as intermediates for preparing optically active tetrahydrofurans useful as optically active moiety in biodegradable polymers, perfumes, intermediates for synthesizing medicines and the like.

ii) Description of the Background Art

Since optically active γ-hydroxyketones can be converted into their corresponding optically active tetrahydrofurans, which are useful as optically active moiety in various compounds, by subjecting them to intramolecular acetalation, they are important as industrial raw materials.

The following two processes have already been known as processes for synthesizing such optically active γ-hydroxyketones.

(i) A process in which an optically active γ-diol is oxidized to obtain its corresponding optically active γ-hydroxyketone.

More specifically, in J. Chem. Soc. Perkin Trans., 2148-2154 (1977), (2R,5R)-2,5-hexanediol is oxidized in the presence of silver carbonate-Celite to obtain (R)-5-hydroxyhexane-2-one in a yield of 46%.

(ii) A process in which nickel chemically modified is used as a catalyst to asymmetrically hydrogenate a γ-diketone, thereby synthesizing its corresponding optically active γ-hydroxyketone.

More specifically, in Bull. Soc. Chem. Belg., 100, 585-595 (1991), 2,5-hexanedione is used to subject it to asymmetric reduction, thereby obtaining (R)-5-hydroxyhexane-2-one in a yield of 78.7% (optical purity: 10.1% ee).

In the process (i), the optically active γ-diol is used as a starting material. The processes for synthesizing this optically active γ-diol were reported in J. Org. Chem. 54, 1755-1756 (1989); Tetrahedron Asymmetry, 7(2), 569 (1991); Tetrahedron Lett. 28(50), 6335-6338 (1987); and Tetrahedron Asymmetry, 3(3), 333-336 (1992). All these processes suffer from such problems that the reaction process takes a long period of time, the yield of the product is poor, and the optical purity of the product is low. On the other hand, the process (ii) can not be used industrially because the optical purity of the product is too low.

SUMMARY OF THE INVENTION

It is an object of the present invention to provide a process for producing optically active γ-hydroxyketones, which is simpler, can minimize in the number of reaction steps and can provide them in a high optical purity.

In view of the foregoing circumstances, the present inventors have paid attention to γ-diketones as starting materials and carried out an extensive investigation as to their asymmetric hydrogenation. As a result, it has been found that when a ruthenium-optically active phosphine complex is used as a catalyst to conduct asymmetric hydrogenation, γ-hydroxyketones can be provided in a high optical purity, thus leading to completion of the present invention.

In an aspect of the present invention, there is thus provided a process for producing a γ-hydroxyketone represented by the following general formula (2):

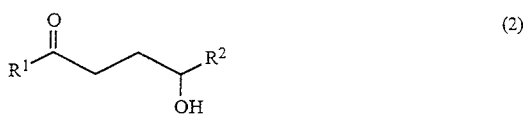

wherein $R^1$ and $R^2$ mean individually an alkyl or phenyl group which may have a substituent group, which comprises asymmetrically hydrogenating a γ-diketone represented by the following general formula (1):

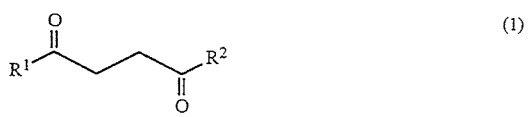

wherein $R^1$ and $R^2$ have the same meaning as defined above, in the presence of a ruthenium-optically active phosphine complex as a catalyst.

According to the present invention, there can be provided an excellent process in which the ruthenium-optically active phosphine complex is used as a catalyst to subject a γ-diketone to an asymmetric hydrogenation, which process is able to efficiently prepare optically active γ-hydroxyketones useful in synthesizing optically active moiety in biodegradable polymers, perfumes, intermediates for synthesizing medicines and the like.

The above and other objects, features and advantages of the present invention will become apparent from the following description and the appended claims.

DETAILED DESCRIPTION OF THE INVENTION AND PREFERRED EMBODIMENTS

In the general formula (1) representing the starting material in the process of the present invention the alkyl groups expressed by $R^1$ and $R^2$ having 1-8 carbon atoms are preferred. Examples of these alkyl groups may include methyl, ethyl, n-propyl, n-butyl, n-pentyl, n-hexyl, n-heptyl and n-octyl groups, etc. Groups which can be substitutable on the alkyl groups may include a phenyl group, alkoxy groups, halogen atoms and the like. Besides, groups which can be substitutable on the phenyl group may include lower alkyl groups, lower alkoxy groups, halogen atoms and the like. Among these lower alkyl or lower alkoxy groups are preferred those having 1-6 carbon atoms. Specific examples of the γ-diketone (1) may include 2,5-hexanedione, 2,5-heptanedione, 2,5-octanedione, 2,5-nonanedione, 2,5-decanedione, 2,5-undecanedione, 2,5-dodecanedione, 2,5-tridecanedione, 3,6-octanedione, 3,6-nonanedione, 3,6-decanedione, 4,7-decanedione, 4,7-dodecanedione, 5,8-undecanedione, 1-phenyl-1,4-pentanedione, 1-phenyl-1,4-hexanedione, 1-phenyl-1,4-heptanedione, 1-phenyl-1,4-octanedione, 1-(p-methoxyphenyl)-1,4-pentanedione, 1-(p-tolyl)-1,4-pentanedione, 1-phenyl-2,5-hexanedione, 1-phenyl-2,5-heptanedione, 1-phenyl-2,5-octanedione, 1-phenyl-2,5-nonanedione, 1-(p-methoxyphenyl)-2,5-hexanedione, 1-(p-tolyl)-2,5-hexanedione, 1,6-diphenyl-2,5-hexanedione, etc.

These γ-diketones (1) can be prepared, for example, by the reaction of an aldehyde and a vinyl ketone as described in Angew. Chem. Int. Ed. Engl., 15(11), 639–712 (1976), or the reaction of an α-keto-acid and a vinyl ketone as described in Chem. ber., 118(3), 1115–1125 (1985).

Examples of the ruthenium-optically active phosphine complex used in the present invention may include those represented by the following general formulae (3), (4), (5) and (6):

  (3)

wherein BIPHOS means a tertiary phosphine represented by the formula (a), (b) or (c):

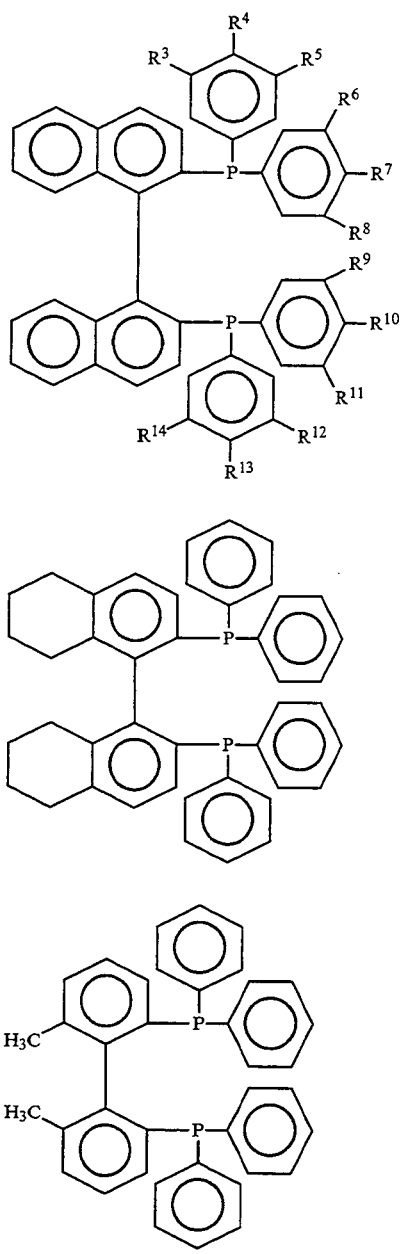

$R^3$, $R^4$, $R^5$, $R^6$, $R^7$, $R^8$, $R^9$, $R^{10}$, $R^{11}$, $R^{12}$, $R^{13}$ and $R^{14}$ individually represent a hydrogen atom, a halogen atom, $C_{1-4}$ alkyl group or $C_{1-4}$ alkoxy group, (s) is a tertiary amine, and x, z and p stand for 2, 4 and 1, respectively, when y is 0, or x, z and p stand for 1, 1 and 0, respectively, when y is 1;

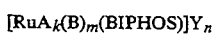  (4)

wherein A means a halogen atom, B denotes benzene which may have a substituent group, or acetonitrile, Y is a halogen atom, $ClO_4$, $PF_6$, $BPh_4$ or $BF_4$, BIPHOS has the same meaning as defined above, and k, m and n stand for 1, 1 and 1, respectively, when B is benzene which may have a substituent group, or m and n stand for 2 and 1, respectively, when B is acetonitrile and k is 1, or m and n stand for 4 and 2, respectively, when B is acetonitrile and k is 0;

  (5)

wherein BIPHOS has the same meaning as defined above; and

  (6)

wherein $R^{15}$ means a hydrogen atom or a lower alkyl group, and BIPHOS has the same meaning as defined above.

Among the above BIPHOS is preferred a tertiary phosphine represented by formula (a).

Examples of the halogen atom represented by $R^3$–$R^{14}$ may include a chlorine atom, a bromine atom, and a fluorine atom, etc., among which a chlorine atom and a fluorine atom are preferred. Examples of the $C_{1-4}$ alkyl group may include methyl group, ethyl group, n-propyl group and t-butyl group, among which methyl group and t-butyl group are preferred.

Examples of the $C_{1-4}$ alkoxy group may include methoxy group, ethoxy group, n-propyloxy group and n-butyloxy group, with methoxy group being preferred.

The lower alkyl group represented by $R^{15}$ having 1–6 carbon atoms are preferred. Examples of the lower alkyl group may include methyl group, ethyl group, n-propyl group, t-butyl group, pentyl group and hexyl group, etc.

Among the tertiary phosphine represented by the above formula (a), is preferred the compound represented by the following formula (a-1):

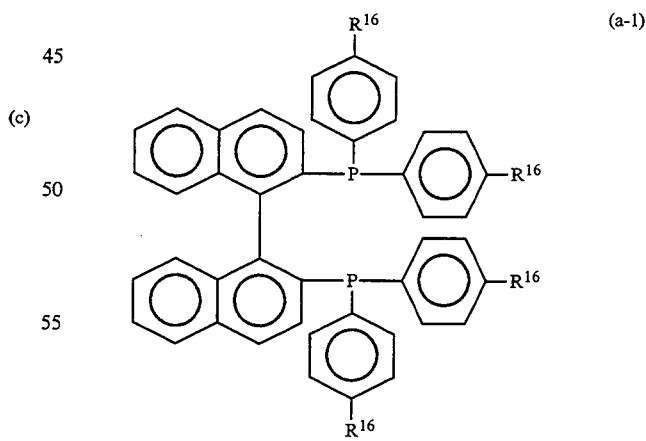

wherein $R^{16}$ represents methyl group or t-butyl group.

The compounds represented by the general formula (3) can be obtained by the processes disclosed in J. Chem. Soc., Chem. Commun., 922–924 (1985), U.S. Pat. No. 4,764,629, U.S. Pat. No. 5,206,399 or U.S. Pat. No. 4,691,037. For example, a complex of the general formula (3), in which y is 0, can be obtained by reacting 1 equivalent mol of [RuCl$_2$(COD)]$_c$ (hereinafter COD stands for 1,5-cyclooctadiene) (c: a natural number), which has been obtained by reacting ruthenium chloride with COD in an ethanol solution, with 1.05–1.2 equivalent mols of BIPHOS such as 2,2′-bis(diphenylphosphino)-1,1′-binaphthyl in the presence of 4 equivalent mols of a tertiary amine such as triethylamine in a solvent such as toluene or ethanol.

The compounds of the general formula (4) can be obtained by the process disclosed in U.S. Pat. No. 4,994,590 or U.S. Pat. No. 5,206,399. For example, complexes in which B is benzene which may have a substituent group (hereinafter abbreviated as "Ar") can be obtained in the following manner. For example, a complex where both A and Y are chlorine atoms, namely, [RuCl(Ar)(BIPHOS)]Cl, can be obtained by using, as a starting material, [RuCl$_2$(Ar)]$_2$ prepared by the process described in J. Org. Chem., 7, 487 (1976) or in Can. J. Chem., 50, 3643 (1972), reacting this compound with BIPHOS at 25°–50° C. for 30 minutes to 3 hours in a single solvent such as methanol, ethanol, benzene or methylene chloride or a mixed solvent thereof and then distilling off the solvent under reduced pressure.

Alternatively, a complex where both A and Y are bromine or iodine atoms, namely, [RuBr(Ar)(BIPHOS)]Br or [RuI(Ar)(BIPHOS)]I, can be obtained quantitatively in the following manner by way of example. [RuCl$_2$(Ar)]$_2$ is used as a starting material to react it with a salt represented by the general formula (7):

$$M^1Z \qquad (7)$$

wherein $M^1$ means a lithium, sodium or potassium atom, and Z denotes a bromine or iodine atom, in the presence of water as a solvent, or react [RuCl$_2$(Ar)]$_2$ with $M^1Z$ at room temperature in a mixed solvent of water and methylene chloride in the presence of a phase-transfer catalyst such as a quaternary ammonium salt or quaternary phosphonium salt represented by the following general formula (8):

$$R^{17}R^{18}R^{19}R^{20}QX \qquad (8)$$

wherein $R^{17}$, $R^{18}$, $R^{19}$ and $R^{20}$ mean individually an alkyl group having 1–16 carbon atoms, phenyl group or benzyl group, Q denotes a nitrogen or phosphorus atom, and X stands for a halogen atom, thereby forming [RuZ$_2$(Ar)]$_2$. In this reaction, a catalyst described in "Phase-Transfer Catalysts", joint authorship of W. P. Weber and G. W. Gokel, joint translation of Iwao Tafuku and Takako Nishitani, published by K.K. Kagakudojin, (Sep. 5, 1978), first edition is used as the phase-transfer catalyst (8). After the resultant [RuZ$_2$(Ar)]$_2$ is then reacted with BIPHOS at 25°–50° C. for 30 minutes to 3 hours in a single solvent such as methanol, ethanol, benzene or methylene chloride or a mixed solvent thereof, the solvent is distilled off under reduced pressure.

Further, in the case where A is a chlorine atom, and Y is ClO$_4$, PF$_6$, BPh$_4$ or BF$_4$ by way of example, the intended complex [RuA(Ar)(BIPHOS)] can be obtained by dissolving [RuCl(Ar)(BIPHOS)]Cl in methanol, ethanol acetone or methylene chloride in advance, adding to the solution a salt represented by M$^2$Y in which M$^2$ means a sodium, potassium, lithium, magnesium or silver atom, and Y denotes a halogen atom, ClO$_4$, PF$_6$, BPh$_4$ or BF$_4$, stirring the resulting mixture and then filtering off a small amount of insoluble matter to concentrate and dry the filtrate.

Among the compounds represented by the general formula (4), complexes where B is acetonitrile can be obtained in the following manner. For example, a complex where both A and Y are chlorine atoms, namely, [RuCl(acetonitrile)$_2$(BIPHOS)]Cl, can be obtained by dissolving a complex [RuCl(Ar)(BIPHOS)]Cl in acetonitrile, refluxing the solution at 50° C. for 10–24 hours to distill off an excess amount of acetonitrile, drying the residue and then recrystallizing the resulting crude complex from methylene chloride.

Besides, a complex [Ru(acetonitrile)$_4$(BipHOS)]Y$_2$ can be obtained, for example, by dissolving a complex [RuCl(Ar)(BIPHOS)]Cl in a mixed solvent of acetonitrile and methanol, ethanol, acetone or methylene chloride in advance, adding M$^2$Y (M$^2$ and Y have the same meaning as defined above) to the solution, heating and stirring the resulting mixture at 25°–50° C. for 10–24 hours, distilling off the solvent, drying the residue and then recrystallizing the resulting crude complex from methylene chloride.

Furthermore, the compounds of the general formula (5) can be obtained by stirring a complex [RuI(p-cymene)(BIPHOS)]I with 3 equivalent mols of iodine at 15°–30° C. for 1–5 hours in a suitable solvent such as methanol, distilling off the solvent and drying the residue, as described in U.S. Pat. No. 5,206,399.

Moreover, the compounds of the general formula (6) can be obtained in the following manner. A compound of the general formula (3), in which x stands for 2, y for 0, z for 2, S for triethylamine and p for 1, namely, a complex Ru$_2$Cl$_4$(BIPHOS)$_2$(triethylamine) is used as a starting material to react the complex with a salt of a carboxylic acid for 3–15 hours at a temperature of about 20°–110° C. in an alcohol solvent such as methanol, ethanol or t-butanol. Thereafter, the solvent is distilled off, and the intended complex is extracted from a solvent such as ether or ethanol and then dried, thereby obtained the complex as a crude product. Further, the crude product can be recrystallized from ethyl acetate or the like to obtain a purified product. In the formula (6), compounds where R$^{15}$ is a lower alkyl can be obtained by varying the kind of the carboxylic acid used. For example, where the above-obtained complex is provided as a starting material, and sodium acetate is used, Ru(OCOCH$_3$)$_2$(BIPHOS) is obtained. Besides, in the case where a complex containing trifluoroacetic acid is prepared, such a complex can be obtained by reacting the diacetate complex obtained in the above-described manner with trifluoroacetic acid at about 25° C. for about 12 hours in methylene chloride as a solvent as described in U.S. Pat. No. 4,739,084, U.S. Pat. No. 4,766,225 or U.S. Pat. No. 5,206,399.

Examples of the above-described complexes may include the following compounds:

Ru$_2$Cl$_4$(BINAP)$_2$(NEt$_3$) in which BINAP means 2,2′-bis(diphenylphosphino)-1,1′-binaphthyl;

Ru$_2$Cl$_4$(T-BINAP)$_2$(NEt$_3$) in which T-BINAP means 2,2′-bis(di-p-tolylphosphino)-1,1′-binaphthyl;

Ru$_2$Cl$_4$(t-Bu-BINAP)$_2$(NEt$_3$) in which t-Bu-BINAP means 2,2′-bis(di-p-tert-butylphenylphosphino)-1,1′-binaphthyl;

Ru$_2$Cl$_4$(p-MeO-BINAP)$_2$(NEt$_3$) in which p-MeO-BINAP means 2,2′-bis(di-p-methoxyphenylphosphino)-1,1′-binaphthyl;

Ru$_2$Cl$_4$(3,5-DiMe-BINAP)$_2$(NEt$_3$) in which 3,5-DiMe-BINAP means 2,2′-bis(di-3,5-xylylphosphino)-1,1′-binaphthyl;

Ru₂Cl₄(3,5-Di-t-Bu-BINAP)₂(NEt₃) in which 3,5-Di-t-Bu-BINAP means 2,2'-bis[di-(3,5-di-tert-butylphenyl)-phosphino]-1,1'-binaphthyl;

Ru₂Cl₄(3-Me-BINAP)₂(NEt₃) in which 3-Me-BINAP means 2,2'-bis(di-m-tolylphosphino)-1,1'-binaphthyl;

Ru₂Cl₄(p-Cl-BINAP)₂(NEt₃) in which p-Cl-BINAP means 2,2'-bis(di-p-chlorophenylphosphino)-1,1'-binaphthyl;

Ru₂Cl₄(p-F-BINAP)₂(NEt₃) in which p-F-BINAP means 2,2'-bis(di-p-fluorophenylphosphino)-1,1'-binaphthyl;

Ru₂Cl₄(MeBIPH)₂(NEt₃) in which MeBIPH means 6,6'-dimethyl-2,2'-bis(diphenylphosphino)-1,1'-biphenyl;

Ru₂Cl₄(BIHNAP)₂(NEt₃) in which BIHNAP means 2,2'-bis(diphenylphosphino)-5,6,7,8,5',6',7',8'-octahydro-1,1'-binaphthyl;

RuHCl(BINAP)₂;
RuHCl(T-BINAP)₂;
RuHCl(t-Bu-BINAP)₂;
RuHCl(p-MeO-BINAP)₂;
RuHCl(3,5-DiMe-BINAP)₂;
RuHCl(3,5-Di-t-Bu-BINAP)₂;
RuHCl(3-Me-BINAP)₂;
RuHCl(p-Cl-BINAP)₂;
RuHCl(p-F-BINAP)₂;
RuHCl(MeBIPH)₂;
RuHCl(BIHNAP)₂;
[RuCl(benzene)(BINAP)]Cl;
[RuCl(benzene)(T-BINAP)]Cl;
[RuCl(benzene)(p-MeO-BINAP)]Cl;
[RuCl(benzene)(3,5-DiMe-BINAP)]Cl;
[RuCl(benzene)(3,5-Di-t-Bu-BINAP)]Cl;
[RuCl(benzene)(3-Me-BINAP)]Cl;
[RuCl(benzene)(p-Cl-BINAP)]Cl;
[RuCl(benzene)(p-F-BINAP)]Cl;
[RuCl(benzene)(MeBIPH)]Cl;
[RuCl(benzene)(BIHNAP)]Cl;
[RuCl(p-cymene)(BINAP)]Cl;
[RuCl(p-cymene)(T-BINAP)]Cl;
[RuCl(p-cymene)(p-MeO-BINAP)]Cl;
[RuCl(p-cymene)(3,5-DiMe-BINAP)]Cl;
[RuCl(p-cymene)(3,5-Di-t-Bu-BINAP)]Cl;
[RuCl(p-cymene)(3-Me-BINAP)]Cl;
[RuCl(p-cymene)(p-Cl-BINAP)]Cl;
[RuCl(p-cymene)(p-F-BINAP)]Cl;
[RuCl(p-cymene)(MeBIPH)]Cl;
[RuCl(p-cymene)(BIHNAP)]Cl;
[RuBr(benzene)(BINAP)]Br;
[RuBr(benzene)(T-BINAP)]Br;
[RuBr(p-cymene)(t-Bu-BINAP)]Br;
[RuBr(p-cymene)(p-MeO-BINAP)]Br;
[RuBr(p-cymene)(3,5-DiMe-BINAP)]Br;
[RuBr(p-cymene)(3,5-Di-t-Bu-BINAP)]Br;
[RuBr(p-cymene)(3-Me-BINAP)]Br;
[RuBr(p-cymene)(p-Cl-BINAP)]Br;
[RuBr(p-cymene)(p-F-BINAP)]Br;
[RuBr(p-cymene)(MeBIPH)]Br;
[RuBr(p-cymene)(BIHNAP)]Br;
[RuI(benzene)(BINAP)]I;
[RuI(benzene)(T-BINAP)]I;
[RuI(benzene)(p-MeO-BINAP)]I;
[RuI(benzene)(3,5-DiMe-BINAP)]I;
[RuI(benzene)(3,5-Di-t-Bu-BINAP)]I;
[RuI(benzene)(3-Me-BINAP)]I;
[RuI(benzene)(p-Cl-BINAP)]I;
[RuI(benzene)(p-F-BINAP)]I;
[RuI(benzene)(MeBIPH)]I;
[RuI(benzene)(BIHNAP)]I;
[RuI(benzene)(t-Bu-BINAP)]I;
[RuI(p-cymene)(BINAP)]I;
[RuI(p-cymene) (T-BINAP)]I;
[RuI(p-cymene) (p-MeO-BINAP)]I;
[RuI(p-cymene) (3,5-DiMe-BINAP)]I;
[RuI(p,cymene) (3,5-Di-t-Bu-BINAP)]I;
[RuI(p-cymene) (3-Me-BINAP)]I;
[RuI(p-cymene) (p-Cl-BINAP)]I;
[RuI(p-cymene) (p-F-BINAP)]I;
[RuI(p-cymene)(MeBIPH)]I;
[RuI(p-cymene)(BIHNAP)]I;
[RuI(p-cymene)(t-Bu-BINAP)]I;
[RuI(methyl benzoate)(BINAP)]I;
[RuI(methyl benzoate)(T-BINAP)]I;
[RuI(methyl benzoate)(t-Bu-BINAP)]I;
[RuI(methyl benzoate)(p-MeO-BINAP)]I;
[RuI(methyl benzoate)(3,5-DiMe-BINAP)]I;
[RuI(methyl benzoate)(3,5-Di-t-Bu-BINAP)]I;
[RuI(methyl benzoate)(3-Me-BINAP)]I;
[RuI(methyl benzoate)(p-Cl-BINAP)]I;
[RuI(methyl benzoate)(p-F-BINAP)]I;
[RuI(methyl benzoate)(MeBIPH)]I;
[RuI(methyl benzoate)(BIHNAP)]I;
[RuCl(benzene)(BINAP)]ClO₄;
[RuCl(benzene)(t-Bu-BINAP)]ClO₄;
[RuCl(benzene)(p-MeO-BINAP)]ClO₄;
[RuCl(benzene)(3,5-DiMe-BINAP)]ClO₄;
[RuCl(benzene)(3,5-Di-t-Bu-BINAP)]ClO₄;
[RuCl(benzene)(3-Me-BINAP)]ClO₄;
[RuCl(benzene)(p-Cl-BINAP)]ClO₄;
[RuCl(benzene)(p-F-BINAP)]ClO₄;
[RuCl(benzene)(MeBIPH)]ClO₄;
[RuCl(benzene)(BIHNAP)]ClO₄;
[RuCl(p-cymene)(BINAP)]PF₆;
[RuCl(p-cymene)(BINAP)]BF₃;
[RuCl(methyl benzoate)(BINAP)]BPh₄;
[Ru(acetonitrile)₄(BINAP)](BF₄)₂;
[RuCl(acetonitrile)₂(BINAP)]Cl;
[RuI(p-cymene)(BINAP)]I₃;
[RuI(p-cymene)(T-BINAP)]I₃;
[RuI(p-cymene)(t-Bu-BINAP)]I₃;
[RuI(p-cymene)(p-MeO-BINAP)]I₃;
[RuI(p-cymene)(3,5-DiMe-BINAP)]I₃;
[RuI(p-cymene)(3,5-Di-t-Bu-BINAP)]I₃;
[RuI(p-cymene)(3-Me-BINAP)]I₃;
[RuI(p-cymene)(p-Cl-BINAP)]I₃;
[RuI(p-cymene)(p-F-BINAP)]I₃;
[RuI(p-cymene)(MeBIPH)]I₃;
[RuI(p-cymene)(BIHNAP)]I₃;
Ru(OCOCH₃)₂(BINAP);
Ru(OCOCH₃)₂(T-BINAP);
Ru(OCOCH₃)₂(t-Bu-BINAP);
Ru(OCOCH₃)₂(p-MeO-BINAP);
Ru(OCOCH₃)₂(3,5-DiMe-BINAP);
Ru(OCOCH₃)₂(3,5-Dit-Bu-BINAP);
Ru(OCOCH₃)₂(3-Me-BINAP);
Ru(OCOCH₃)₂(p-Cl-BINAP);
Ru(OCOCH₃)₂(p-F-BINAP);
Ru(OCOCH₃)₂(MeBIPH);
Ru(OCOCH₃)₂(BIHNAP);
Ru(OCOCF₃)₂(BINAP);
Ru(OCOCF₃)₂(T-BINAP);
Ru(OCOCF₃)₂(t-Bu-BINAP);
Ru(OCOCF₃)₂(p-MeO-BINAP);
Ru(OCOCF₃)₂(3,5-DiMe-BINAP);

Ru(OCOCF$_3$)$_2$(3,5-Di-t-Bu-BINAP);
Ru(OCOCF$_3$)$_2$(3-Me-BINAP);
Ru(OCOCF$_3$)$_2$(p-Cl-BINAP);
Ru(OCOCF$_3$)$_2$(p-F-BINAP);
Ru(OCOCF$_3$)$_2$(MeBIPH);
Ru(OCOCF$_3$)$_2$(BIHNAP);

In the practice of the present invention, the γ-diketone (1) is dissolved in a single protic solvent such as methanol, ethanol or isopropyl alcohol, a single solvent such as tetrahydrofuran or acetone, a mixed solvent thereof, or a solvent with a small amount of water added thereto (preferably, methanol or ethanol). The resulting solution is placed in an autoclave and added with the ruthenium-optically active phosphine complex to subject the diketone to an asymmetric hydrogenation, thereby obtaining a desired γ-hydroxyketone. And, ruthenium-optically active phosphine complexes utilized in the present invention is prepared in situ. For Example, both precursor of the complexes such as [RuCl$_2$(COD)]$_c$, [RuCl$_2$(Ar)]$_2$ and BIPHOS are added to the suitable solvents in the reactant independently, followed by the γ-diketone is added to the mixture. When the configuration of the optically active phosphine complex used in the present invention is suitably changed to (R) or (S), a γ-hydroxyketone having a desired configuration can be obtained. The hydrogenation is conducted by adding the catalyst in a proportion of 1/50 to 1/5000 mol, preferably 1/100 to 1/1000 mol, per mole of the γ-diketone (1) and stirring the reaction mixture at a reaction temperature of 5°–100° C., preferably 30°–50° C. for 1–72 hours, preferably 8–20 hours under a hydrogen pressure of 5–50 kg/cm$^2$, preferably 30–50 kg/cm$^2$. After completion of the reaction, isolation of the product is conducted by distilling off the solvent, and then distilling the residue under reduced pressure, or treating it by column chromatography on a silica gel, thereby obtaining the intended optically active γ-hydroxyketone in a yield of 50–90%.

The present invention will hereinafter be described in more detail by the following examples. However, it should be borne in mind that this invention is not limited to and by these examples only.

Incidentally, the analytical values in the examples were obtained by using the following analytic instruments:

Gas chromatograph: HITACHI 263-80 (manufactured by Hitachi, Ltd.)
Column: Silicon OV-101, silica capillary, 0.25 mm across, 25 m long (manufactured by GL Science K.K.)
HEWLETT PACKARD 5890 SERIES II (manufactured by HEWLETT PACKARD Co.)
Column: NEUTRABOND 1, silica capillary, 0.25 mm across, 25 m long
Measuring temperature:
50°–150° C. (initial temperature),
1°–10° C./min (heating rate)
High performance liquid chromatograph (hereinafter abbreviated as "HPLC":
665-A-11 (manufactured by Hitachi, Ltd.)
Column: COSMOSIL 5SL, 4.6 mm across, 250 mm long (manufactured by NACALAI TESQUE INC.)
Developing solvent:
Hexane/ether (8/1 to 10/1),
0.5–1.5 ml/min
Detector: UV Detector 635M (UV-254 nm) (manufactured by Hitachi, Ltd.)
$^1$H-Nuclear magnetic resonance spectrum (hereinafter abbreviated as "$^1$H-NMR") analyzer:
AM-400 Model (400 MHz) (manufactured by BRUKER INC.)
Internal standard substance: Tetramethylsilane
Optical rotation: DIP-4 Model (manufactured by Japan Spectroscopic Co., Ltd.)

Example 1

Synthesis of (−)-5-hydroxyhexane-2-one:

A 100-ml stainless steel autoclave purged with nitrogen in advance was charged with 5 g (0.0438 mol) of 2,5-hexanedione and 10 ml of methanol. A solution of 0.197 g (0.109 mmol) of Ru$_2$Cl$_4$((R)-T-BINAP)$_2$(NEt$_3$) in 2 ml of methylene chloride was added thereto, thereby conducting reaction at a reaction temperature of 50° C. for 8 hours under a hydrogen pressure of 50 kg/cm$^2$. After distilling off the solvent, the residue was purified by column chromatography on a silica gel using a developing solvent of hexane/ethyl acetate (5/1) to obtain 4.35 g of (−)-5-hydroxyhexane-2-one (yield: 85.6%).

$^1$H-NMR (CDCl$_3$)δppm: 1.2(3H,d), 1.68–1.76(2H,m), 2.1(3H,s), 2.6(2H,m), 3.8(1H,m).

[α]$_D^{25}$: −10.09 (C=1.03 ethanol)

An ester was synthesized from the thus-obtained hydroxyketone and (R)- or (S)-α-methoxy-α-trifluoromethylphenylacetic acid (hereinafter abbreviated as "MTPA") to analyze it by HPLC making use of a developing solvent of hexane/ether (9/1). As a result, the hydroxyketone was found to have an optical purity of 100% ee.

Examples 2–8

The procedures in Example 1 were followed except that the catalyst and reaction conditions in Example 1 were changed. The results are shown in Table 1.

TABLE 1

| Ex. | Catalyst | Substrate/catalyst (molar ratio) | Temperature (°C.) | Time (hrs) | Yield (%) | Optical purity (% ee) |
|---|---|---|---|---|---|---|
| 2 | Ru$_2$Cl$_4$[(R)-T-BINAP]$_2$NEt$_3$ | 400 | 50 | 8 | 85.9 | 99.6 |
| 3 | [RuI(C$_6$H$_6$){(R)-T-BINAP}]I | 100 | 50 | 12 | 78.6 | 96.3 |
| 4 | Ru$_2$Cl$_4$[(R)-BINAP]$_2$NEt$_3$ | 200 | 50 | 9 | 86.1 | 99.5 |
| 5 | RuHCl[(RO-t-Bu-BiNAP]$_2$ | 50 | 80 | 12 | 52.4 | 87.3 |
| 6 | [RuCl(C$_6$H$_5$CO$_2$CH$_3$){(R)-BINAP}]BPh$_4$ | 50 | 80 | 20 | 48.2 | 83.5 |
| 7 | [RuCl(CH$_3$CN)$_2${(RO-BINAP}]Cl | 50 | 80 | 16 | 43.5 | 82.7 |
| 8 | Ru(OCOCF$_3$)$_2$[(R)-t-Bu-BINAP] | 50 | 80 | 14 | 38.4 | 78.4 |

Example 9

Synthesis of (−)-4-hydroxy-1-phenylpentane-1-one:

A 100-ml stainless steel autoclave purged with nitrogen in advance was charged with 5 g (0.0284 mol) of 5-phenyl-2,5-pentanedione and 10 ml of methanol. A solution of 0.2 g (0.142 mmol) of [RuI(p-cymene)((R)-

T-BINAP)]I₃ in 2 ml of methylene chloride was added thereto, thereby conducting reaction at a reaction temperature of 50° C. for 40 hours under a hydrogen pressure of 50 kg/cm². After distilling off the solvent, the residue was purified by column chromatography on a silica gel using a developing solvent of hexane/ethyl acetate (5/1) to obtain 4.5 g of (−)-4-hydroxy-1-phenyl-pentane-1-one (yield: 90.0%).

¹H-NMR (CDCl₃)δppm: 1.26(2H,d,J=6Hz), 1.7–1.9(2H,m), 3.148,3.15(2H,dt,J=7.08Hz), 3.9(1H,m), 7.46(2H,m), 7.55(1H,m), 7.98(2H,m).

$[\alpha]_D^{25}$: −14.31 (C=1.02 ethanol)

An ester was synthesized from the thus-obtained hydroxyketone and (R)- or (S)-MTPA to analyze it by HPLC making use of a developing solvent of hexane/ether (9/1). As a result, the hydroxyketone was found to have an optical purity of 99.6% ee.

Examples 10–16

The procedures in Example 9 were followed except that the catalyst and reaction conditions in Example 1 were changed. The results are shown in Table 2.

TABLE 2

| Example | Catalyst | Solvent | Yield (%) | Optical purity (% ee) |
|---|---|---|---|---|
| 10 | Ru₂Cl₄[(R)-T-BINAP]₂NEt₃ | MeOH | 74.6 | 94.5 |
| 11 | Ru₂Cl₄[(R)-T-BINAP]₂NEt₃ | EtOH | 74.3 | 94.4 |
| 12 | [RuI(p-cymene){(R)-T-BINAP}]I | MeOH | 86.9 | 97.3 |
| 13 | [RuI(p-cymene){(R)-T-BINAP}]I | MeOH/H₂O (10/1) | 56.8 | 87.3 |
| 14 | [RuI(p-cymene){(R)-T-BINAP}]I | MeOH/CH₂Cl₂ (1/1) | 19.3 | 95.3 |
| 15 | [RuI(p-cymene){(R)-T-BINAP}]I | MeCO/H₂O (10/1) | 83.7 | 92.8 |
| 16 | [RuI(p-cymene){(R)-T-BINAP}]I₃ | MeOH/H₂O (10/1) | 89.5 | 96.7 |

Example 17

Synthesis of (−)-2-hydroxynonane-5-one:

A 100-ml stainless steel autoclave purged with nitrogen in advance was charged with 5 g (0.032 mol) of 2,5-nonanedione and 10 ml of methanol. A solution of 0.144 g (0.08 mmol) of Ru₂Cl₄((R)-T-BINAP)₂(NEt₃) in 2 ml of methylene chloride was added thereto, thereby conducting reaction at a reaction temperature of 50° C. for 20 hours under a hydrogen pressure of 50 kg/cm². After distilling off the solvent, the residue was purified by column chromatography on a silica gel using a developing solvent of hexane/ethyl acetate (4/1) to obtain 3.3 g of (−)-2-hydroxynonane-5-one (yield: 65.6%).

¹H-NMR (CDCl₃)δppm: 0.9(3H,t,J=7.4 Hz), 1.2(3H,d,J=6.2 Hz), 1.3(2H,m), 1.55–1.78(3H,m), 2.43(2H,t,J=7.6 Hz), 2.56(2H,t,J=7Hz), 3.8(1H,m).

$[\alpha]_D^{25}$: −10.19 (C=1.05 ethanol)

An ester was synthesized from the thus-obtained alcohol and (R)- or (S)-MTPA to analyze it by HPLC making use of a developing solvent of hexane/ether (95/5). As a result, the hydroxyketone was found to have an optical purity of 99.8% ee.

Example 18

Synthesis of (−)-5-hydroxy-6-phenylhexane-2-one:

A 100-ml stainless steel autoclave purged with nitrogen in advance was charged with 5 g (0.0261 mol) of 6-phenyl-2,5-hexanedione and 10 ml of methanol. A solution of 0.185 g (0.13 mmol) of RuI(p-cymene)((R)-T-BINAP)]I₃ in 2 ml of methylene chloride was added thereto, thereby conducting reaction at a reaction temperature of 50° C. for 36 hours under a hydrogen pressure of 50 kg/cm². After distilling off the solvent, the residue was purified by column chromatography on a silica gel using a developing solvent of hexane/ethyl acetate (5/1) to obtain 3.03 g of (−)-5-hydroxy-6-phenylhexane-2-one (yield: 60.2%).

¹H-NMR (CDCl₃)δppm: 1.72(1H,m), 1.87(1H,m), 2.16(3H,s), 2.625,2.633(2H,dt,J=7 Hz), 2.69,2.71(1H,dd,J=13.6 Hz), 2.811,2.823(1H,dd,J=13.6 Hz).

$[\alpha]_D^{25}$: −3.57 (C=1.05 ethanol)

An ester was synthesized from the thus-obtained alcohol and (R)- or (S)-MTPA to analyze it by HPLC making use of a developing solvent of hexane/ether (8/2). As a result, the hydroxyketone was found to have an optical purity of 68.5% ee.

What is claimed is:

1. A process for producing a γ-hydroxyketone having the formula (2)

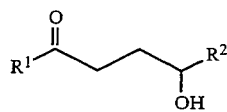
(2)

wherein R¹ and R² are, individually, C₁₋₈-alkyl, C₁₋₈-alkyl substituted with phenyl, halogen or alkoxy groups, phenyl, or phenyl substituted with halogen, lower alkyl or lower alkoxy groups, comprising:

asymmetrically hydrogenating a γ-diketone having the formula (1)

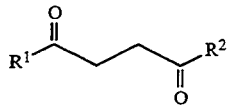
(1)

wherein R¹ and R² have the same meaning as defined above, in the presence of a ruthenium-optically active phosphine complex catalyst, said catalyst having the formula (4)

{RuA_k(B)_m(BIPHOS)}Y_n          (4)

wherein BIPHOS is a tertiary phosphine having the formula (a), (b) or (c)

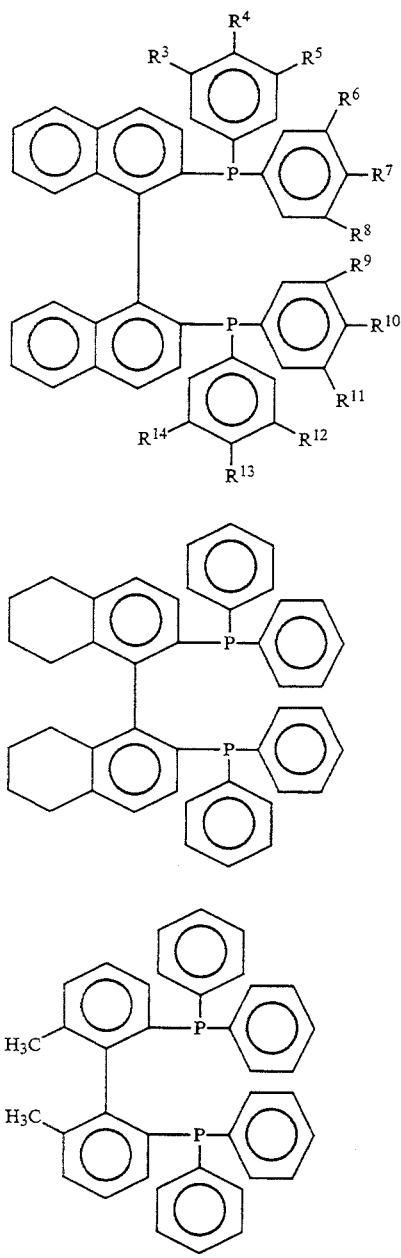

(a)

(b)

(c)

wherein $R^3$, $R^4$, $R^5$, $R^6$, $R^7$, $R^8$, $R^9$, $R^{10}$, $R^{11}$, $R^{12}$, $R^{13}$ and $R^{14}$, individually, are a hydrogen atom, a halogen atom, a $C_{1-4}$ alkyl group or a $C_{1-4}$ alkoxy group, A is a halogen atom, B is acetonitrile, benzene or methylbenzoate, Y is a halogen atom, $ClO_4$, $PF_6$, $BPh_4$ or $BF_4$; where k, m and n are 1,1 and 1, respectively, when B is benzene or methylbenzoate; m and n are 2 and 1, respectively, when B is acetonitrile and k is 1; and m and n are 4 and 2, respectively, when B is acetonitrile and k is 0; or a catalyst having the formula (5)

$$\{RuI(\text{p-cymene)(BIPHOS)}\}I_3 \quad (5)$$

wherein BIPHOS is a tertiary phosphine having said formula (a), (b) or (c) defined above; or a catalyst having the formula (6)

$$Ru(OCO\text{-}R^{15})_2(BIPHOS) \quad (6)$$

wherein $R^{15}$ is a hydrogen atom, trifluoromethyl, or a lower alkyl group, and BIPHOS is a tertiary phosphine having said formula (b) or (c) defined above, or a catalyst having formula (3)

$$Ru_xH_yCl_z(BIPHOS)_2(S)_p \quad (3)$$

wherein BIPHOS is a tertiary phosphine having said formula (b) or (c), (S) is a tertiary amine; where x, z and p are 2,4 are 1, respectively, when y is zero; and x, z and p are 1,1 and 0, respectively, when y is 1.

2. The process of claim 1, wherein said catalyst has formula (4).

3. The process of claim 2, wherein said BIPHOS has formula (a).

4. The process of claim 1, wherein said catalyst has formula (5).

5. The process of claim 4, wherein said BIPHOS has formula (a).

6. The process of claim 1, wherein said catalyst has formula (6).

7. The process of claim 1, wherein said catalyst has formula (3).

8. The process of claim 1, wherein said hydrogenating step is conducted at a temperature of 5°–100° C. for 1–72 hours under a hydrogen pressure of 5–50 kg/cm².

9. The process of claim 8, wherein said temperature is 30°–50° C.

10. The process of claim 8, wherein said hydrogenating step is conducted for 8–20 hours.

11. The process of claim 8, wherein said hydrogen pressure is 30–50 kg/cm².

12. The process of claim 8, wherein said catalyst is used in a proportion of 1/50 to 1/5000 mol per mole of said γ-diketone.

13. The process of claim 12, wherein said catalyst is used in a proportion of 1/100 to 1/1000 mol per mole of said γ-diketone.

14. The process of claim 1, wherein said γ-hydroxyketone is produced with an optical purity of 78.4–100% ee.

* * * * *